United States Patent
Ohashi

(10) Patent No.: US 10,223,765 B2
(45) Date of Patent: Mar. 5, 2019

(54) INFORMATION PROCESSING APPARATUS, INFORMATION PROCESSING METHOD, AND PROGRAM

(71) Applicants: Sony Corporation, Tokyo (JP); Japanese Foundation For Cancer Research, Tokyo (JP)

(72) Inventor: Takeshi Ohashi, Kanagawa (JP)

(73) Assignees: Sony Corporation (JP); Japanese Foundation For Cancer Research (JP)

(*) Notice: Subject to any disclaimer, the term of this patent is extended or adjusted under 35 U.S.C. 154(b) by 35 days.

(21) Appl. No.: 14/424,222

(22) PCT Filed: Aug. 23, 2013

(86) PCT No.: PCT/JP2013/072594
§ 371 (c)(1),
(2) Date: Feb. 26, 2015

(87) PCT Pub. No.: WO2014/038408
PCT Pub. Date: Mar. 13, 2014

(65) Prior Publication Data
US 2015/0228053 A1 Aug. 13, 2015

(30) Foreign Application Priority Data
Sep. 6, 2012 (JP) .................. 2012-196008

(51) Int. Cl.
*G06T 3/00* (2006.01)
*G06T 5/50* (2006.01)
(Continued)

(52) U.S. Cl.
CPC .......... *G06T 3/0006* (2013.01); *G02B 21/365* (2013.01); *G06F 19/00* (2013.01);
(Continued)

(58) Field of Classification Search
CPC .... A61B 6/5217; A61B 6/5294; A61K 38/00; G06F 19/321; G06T 11/00; G06T 2207/20212; G06T 3/0006; G06T 5/50
See application file for complete search history.

(56) References Cited

U.S. PATENT DOCUMENTS 8,643,671 B2 2/2014 Wakita et al.
2003/0095178 A1* 5/2003 Shibayama ........ H04N 13/0025
348/46
(Continued)

FOREIGN PATENT DOCUMENTS

CN 102129505 A 7/2011
EP 1583024 A2 10/2005
(Continued)

OTHER PUBLICATIONS

Extended European Search Report for Application No. 13834573.1 dated Mar. 23, 2016.
(Continued)

*Primary Examiner* — Sing-Wai Wu
(74) *Attorney, Agent, or Firm* — Lerner, David, Littenberg, Krumholz & Mentlik, LLP

(57) ABSTRACT

Provided is an information processing apparatus including an image supply unit that supplies a plurality of input images showing corresponding objects to an image processing unit and obtains a plurality of object images as an image processed result from the image processing unit, and a display control unit that synchronously displays the plurality of object images that have been obtained. The object images are regions including the corresponding objects extracted from the plurality of input images, and orientations, positions, and sizes of the corresponding objects of the plurality of object images are unified.

1 Claim, 17 Drawing Sheets

(51) Int. Cl.
*G06T 11/00* (2006.01)
*G02B 21/36* (2006.01)
*G06F 19/00* (2018.01)
*A61B 6/00* (2006.01)

(52) U.S. Cl.
CPC .............. *G06F 19/321* (2013.01); *G06T 5/50* (2013.01); *G06T 11/00* (2013.01); *A61B 6/5217* (2013.01); *A61B 6/5294* (2013.01); *G06T 2207/20212* (2013.01)

(56) References Cited

U.S. PATENT DOCUMENTS

| | | | | |
|---|---|---|---|---|
| 2003/0199762 | A1* | 10/2003 | Fritz | A61B 8/0858 600/437 |
| 2005/0013471 | A1* | 1/2005 | Snoeren | G06T 7/0034 382/131 |
| 2010/0194971 | A1* | 8/2010 | Li | G02B 7/38 348/349 |
| 2011/0243405 | A1* | 10/2011 | Ohashi | G06K 9/0014 382/128 |
| 2012/0087556 | A1* | 4/2012 | Dai | G06K 9/0014 382/128 |

FOREIGN PATENT DOCUMENTS

| | | |
|---|---|---|
| EP | 2333717 A1 | 6/2011 |
| JP | 09-281405 A | 10/1997 |
| JP | 2007-024927 A | 2/2007 |
| JP | 2011-118005 A | 6/2011 |
| JP | 2013-174823 A | 9/2013 |
| WO | 2012043499 A1 | 4/2012 |

OTHER PUBLICATIONS

International Search Report from International Publication No. PCT/JP2013/072594 dated Sep. 24, 2013.
Chinese Office Action for Application No. 201380044927.9, dated May 27, 2017.
Japanese Office Action for Application No. 2014-534285, dated Sep. 26, 2017.
Chinese Office Action for Application No. 201380044927.9, dated Jul. 2, 2018.

* cited by examiner

A          B

FIG. 11
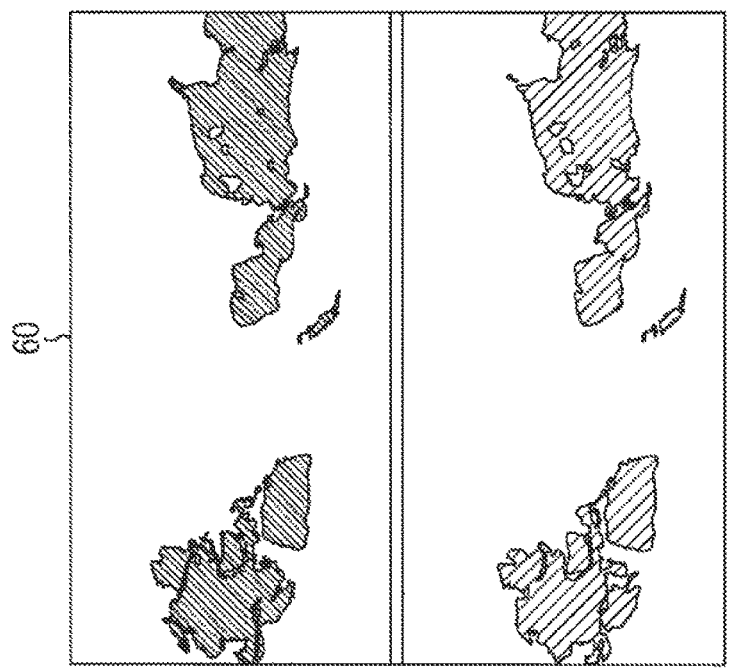
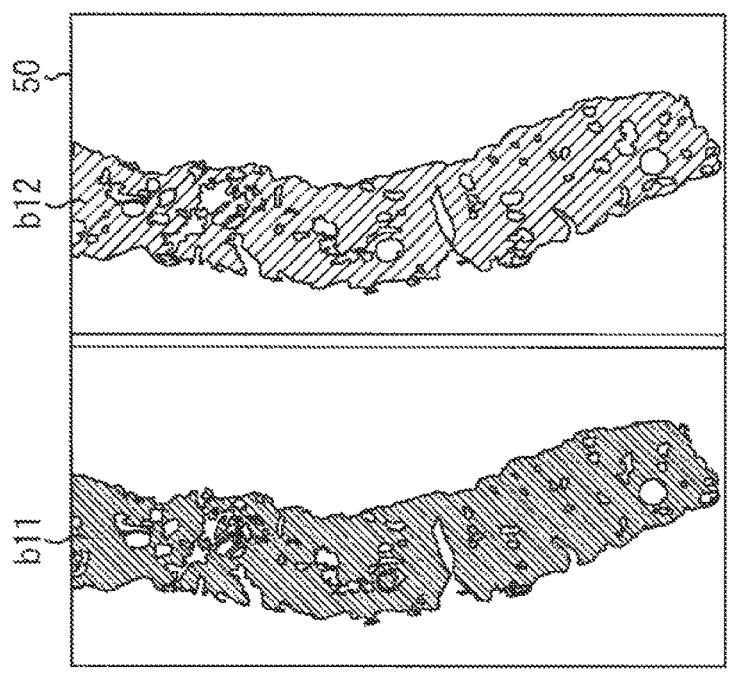
AUTOMATIC VERTICAL/HORIZONTAL
DIVISION SELECTION DISPLAY FIG. 13
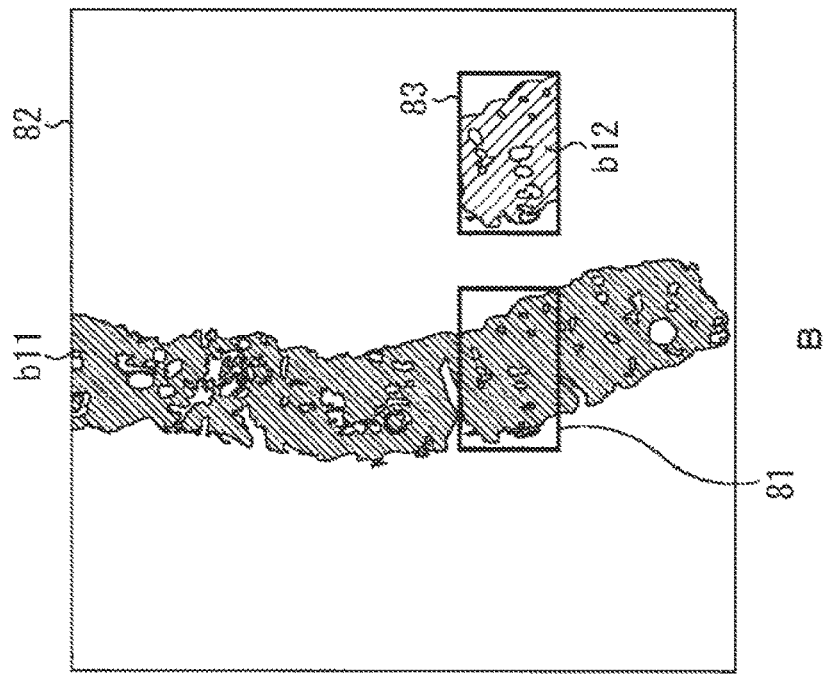
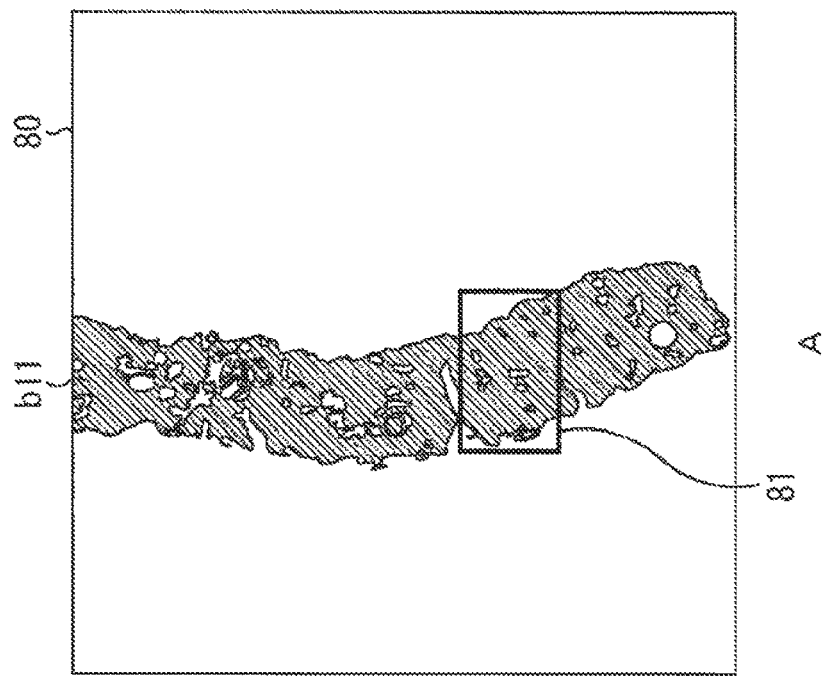
CUT AND ARRANGEMENT DISPLAY

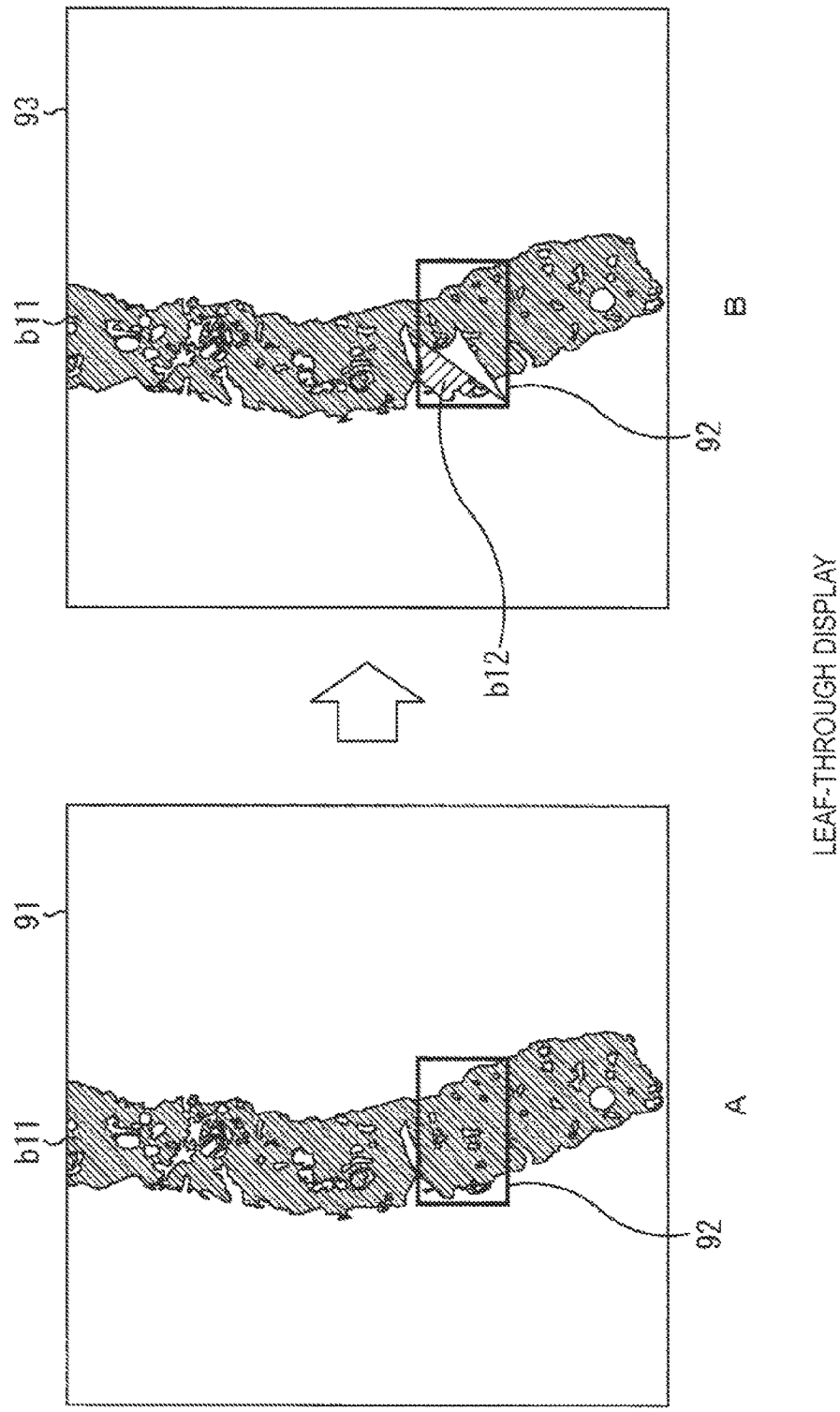

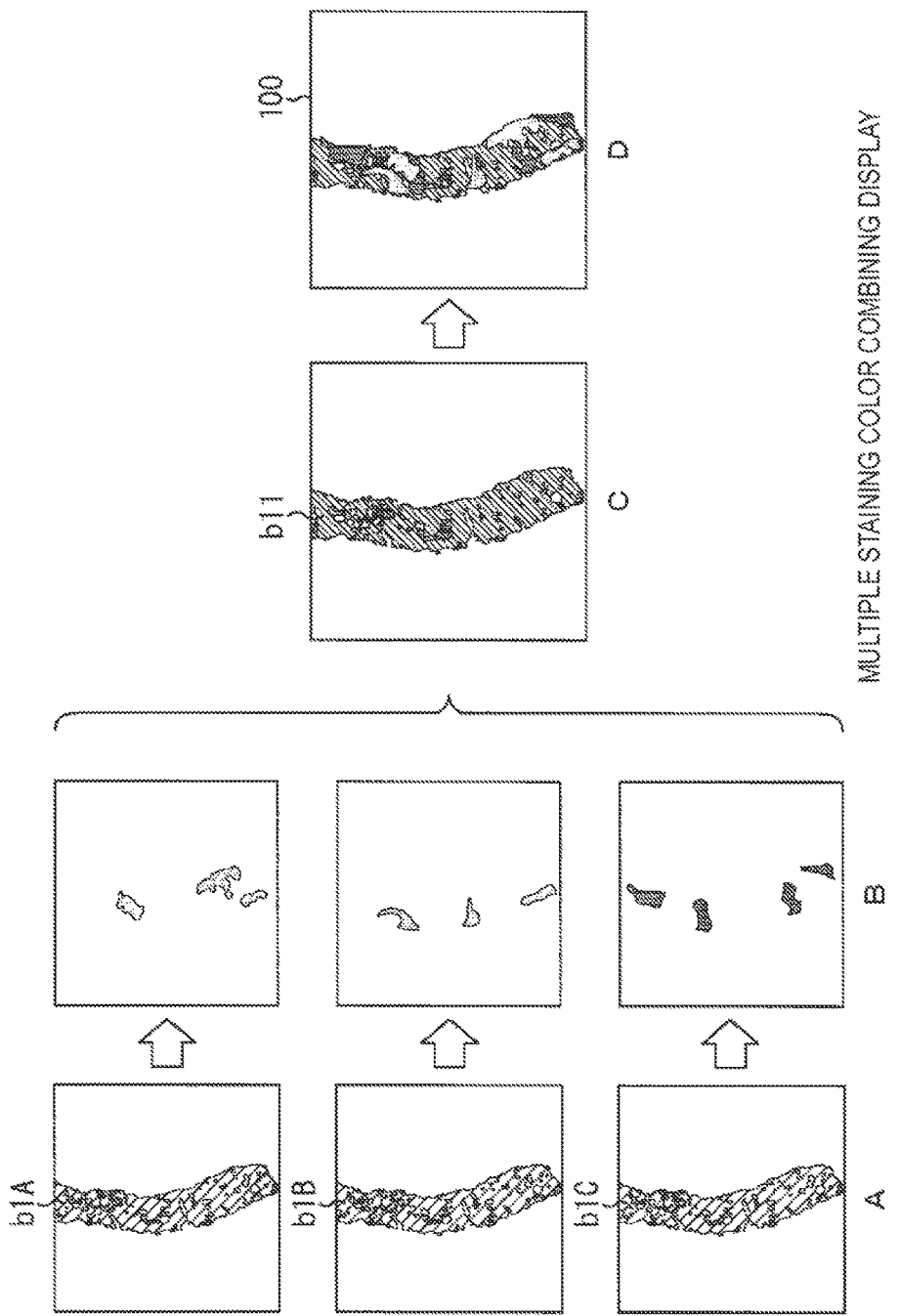

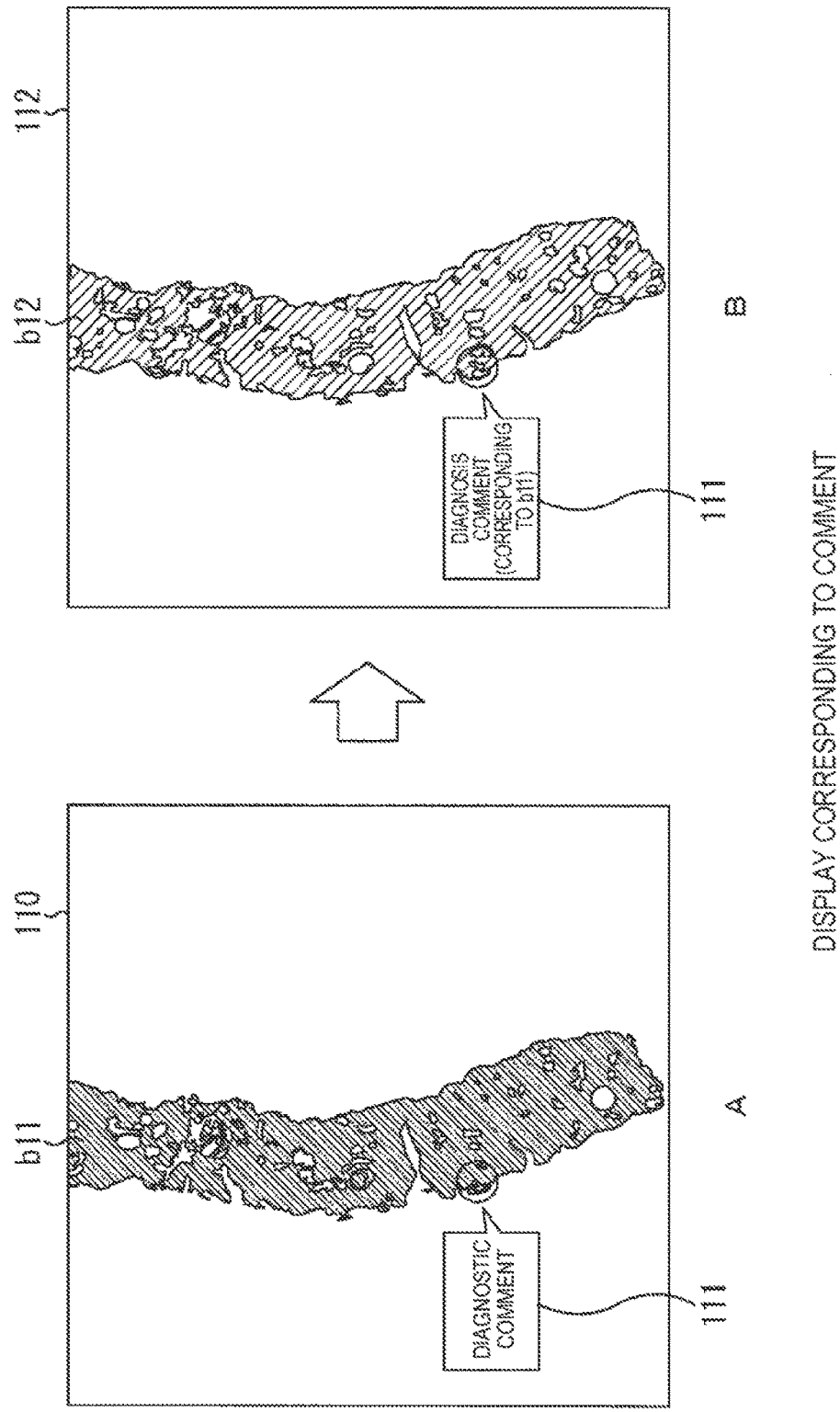

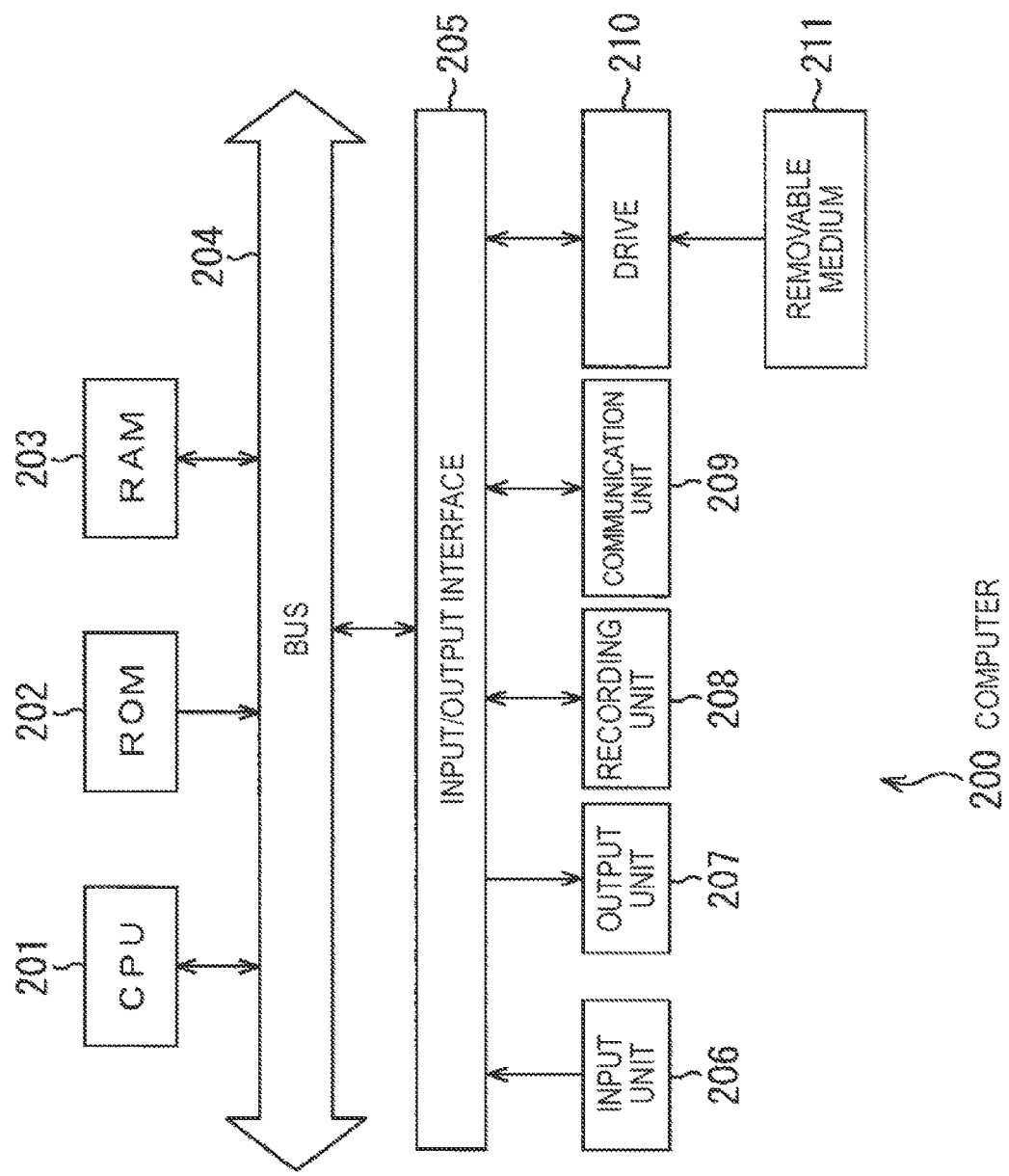

INFORMATION PROCESSING APPARATUS, INFORMATION PROCESSING METHOD, AND PROGRAM

CROSS-REFERENCE TO RELATED APPLICATION

The present application is a national phase entry under 35 U.S.C. § 371 of International Application No. PCT/JP2013/072594 filed Aug. 23, 2013, published on Mar. 13, 2014 as WO 2014/038408 A1, which claims priority from Japanese Patent Application No. JP 2012-196008 filed in the Japanese Patent Office on Sep. 6, 2012.

TECHNICAL FIELD

The present disclosure relates to an information processing apparatus, an information processing method, and a program, in particular, to an information processing apparatus, an information processing method, and a program that are suitable for simultaneously displaying a plurality of pathological images so as to comparatively perform pathologic diagnosis.

BACKGROUND ART

At ordinary health care sites, as methods that diagnose pathological tissues such as tumors (for example, diagnose whether a pathological tissue is a malignant tumor such as a cancer), a prepared specimen is made in such a manner that part of a pathological tissue is harvested from the patient, the harvested pathological tissue is sliced, the sliced tissue (hereinafter referred to as a biopsy) is placed on a slide glass, and then the biopsy is stained. The prepared specimen is observed and diagnosed under a microscope or the like.

The following relationships of staining methods (such as reagents), staining targets, and staining colors are known.

| Staining Method | Staining Target | Color |
| --- | --- | --- |
| Hematoxylin | cell nucleus | bluish purple |
| Eosin | cell nucleus, connective tissue | light red |
| PAS staining | mucus | purple |
| KB staining | nerve fiber | blue |
| Keratin 903 | basal cell | brown |

Besides above staining methods, Hematoxylin & Eosin (H&E), Immunohistochemistry (IHC), Fluorescence In Situ Hybridization (FISH), and so forth are known.

H&E can be used to stain basophilic cell nucleus, bony tissue, part of cartilaginous tissue, serum component, and so forth in bluish purple; and acidophilic cytoplasm, connective tissue of soft tissue, erythrocyte, fibrin, endocrine granule, and so forth in red pink.

IHC can be used to visualize an antigen-antibody reaction. FISH can be used to map a gene and detect chromosome aberrations.

Thus, since these staining methods deal with different staining targets, when different staining methods are applied to the same part of the tissue and the resultant part is observed, diagnosis can be more accurately perform than one staining method is applied.

However, if a sliced tissue on one prepared specimen is stained by a plurality of different staining methods, since stained colors are not properly developed, the diagnosis is likely to become difficult. In addition, some staining methods may not be used together. Thus, it is preferred to prevent a plurality of staining colors from co-existing on one prepared specimen.

FIG. 1 shows an example prepared specimen that has been made. A prepared specimen P1 shown in FIG. 1A and a prepared specimen P2 shown in FIG. 1B are composed of biopsies adjacently cut from a harvested pathological tissue. For example, it is assumed that one of the prepared specimens P1 and P2 is stained by H&E, the other is stained by IHC.

A biopsy b11 at the left end on the prepared specimen P1 shown in FIG. 1A and a biopsy b12 at the left end on the prepared specimen P2 shown in FIG. 1B are adjacently cut from the pathological tissue that is punctured and harvested. Hereinafter, the relationship between the biopsy b11 and the biopsy b21 is referred to as corresponding biopsies. Likewise, the relationship between a biopsy b21 at the center of FIG. 1A and a biopsy b22 at the center of FIG. 1B and the relationship between a biopsy b31 at the right end of FIG. 1A and a biopsy b32 at the right end of FIG. 1B are also respectively referred to as corresponding biopsies.

Rectangle frames on the prepared specimens P1 and P2 represent regions on the same coordinates on the prepared specimens P1 and P2. When the prepared specimens P1 and P2 are compared, it is obvious that corresponding biopsies on the two prepared specimens P1 and P2 are not always located on the same coordinates. In addition, when a biopsy is cut, the shape of the biopsy may be deformed depending on the cutting force and so forth applied to the biopsy.

As the simplest method that compares the two prepared specimens P1 and P2, quickly moving the observing positions of the two prepared specimens P1 and P2 simultaneously placed under a microscope, a diagnostician such as a pathologist looks for corresponding portions and performs diagnosis. In this case, however, if the diagnostician moves the prepared specimens excessively or insufficiently, it is difficult for him or her to accurately and efficiently observe the corresponding portions.

Thus, as a method that does not cause the diagnostician to move the prepared specimens, a virtual microscope system has been proposed (for example, see Patent Literature 1 below).

The virtual microscope system divides a diagnosing biopsy on a prepared specimen into small regions, photographs the divided small regions through an objective lens having a high resolution, and combines the plurality of small regions so as to reconstruct the image of the diagnosing biopsy as digital image data.

When two prepared specimens are reconstructed as digital image data by the virtual microscope system, the two prepared specimens can be simultaneously displayed on a screen or the like of a personal computer.

CITATION LIST

Patent Literature

Patent Literature 1: JP H09-281405A

SUMMARY OF INVENTION

Technical Problem

However, even if such a virtual microscope system is used to accurately and simultaneously display corresponding portions on two prepared specimens, the diagnostician still needs to perform operations of the system including an enlargement operation, a reduction operation, and a rotation operation for images.

The present disclosure is made from the foregoing point of view such that corresponding portions of a plurality of images are accurately and simultaneously displayed.

Solution to Problem

An information processing apparatus according to an aspect of the present disclosure includes an image supply unit that supplies a plurality of input images showing corresponding objects to an image processing unit and obtains a plurality of object images as an image processed result from the image processing unit, and a display control unit that synchronously displays the plurality of object images that have been obtained. The object images are regions including the corresponding objects extracted from the plurality of input images, and orientations, positions, and sizes of the corresponding objects of the plurality of object images are unified.

The display control unit may execute at least one of a guide scroll display, an automatic vertical/horizontal division selection display, an instantaneous switch display, a cut and placement display, a leaf-through display, and a multiple staining color combining display.

The plurality of images may be medical images.

The objects may be biopsies cut from a tissue. The plurality of medical images may be pathological images that are scanned from prepared specimens of which the biopsies adjacently cut from a same tissue and placed on slide glasses and stained by different staining methods.

The image processing unit may be a server located on Internet.

The information processing apparatus according to an aspect of the present disclosure may further include the image processing unit.

An information processing method according to an aspect of the present disclosure performed by an information processing apparatus includes supplying a plurality of input images showing corresponding objects to an image processing unit, obtaining a plurality of object images as an image processed result from the image processing unit, and synchronously displaying the plurality of object images that have been obtained. The object images are regions including the corresponding objects extracted from the plurality of input images, and orientations, positions, and sizes of the corresponding objects of the plurality of object images are unified.

A program according to an aspect of the present disclosure for causing a computer to function as an image supply unit that supplies a plurality of input images showing corresponding objects to an image processing unit and obtains a plurality of object images as an image processed result from the image processing unit, and a display control unit that synchronously displays the plurality of object images that have been obtained. The object images are regions including the corresponding objects extracted from the plurality of input images, and orientations, positions, and sizes of the corresponding objects of the plurality of object images are unified.

According to an aspect of the present disclosure, a plurality of input images that show corresponding objects are supplied to an image processing unit, a plurality of object images are obtained as an image processed result of the image processing unit, and the plurality of the obtained object images are synchronously displayed.

BRIEF DESCRIPTION OF DRAWINGS

FIG. 11 is a schematic diagram showing an example screen shot of an automatic vertical/horizontal division selection display.

FIG. 13 is a schematic diagram showing an example screen shot of a cut and placement display.

FIG. 14 is a schematic diagram showing an example screen shot of a leaf-through display.

FIG. 15 is a schematic diagram showing an example screen shot of a multiple staining color combining display.

FIG. 16 is a schematic diagram showing an example screen shot of a relevant comment display.

FIG. 17 is a block diagram showing an example configuration of a computer.

DESCRIPTION OF EMBODIMENTS

Hereinafter, preferred embodiments of the present disclosure will be described in detail with reference to the appended drawings. Note that, in this specification and the drawings, elements that have substantially the same function and structure are denoted with the same reference signs, and repeated explanation is omitted.

[Example Configuration of Pathological Image Display Control Device]

A pathological image display control device corresponds to an information processing apparatus according to an embodiment of the present disclosure. The pathological image display control device accurately and simultaneously displays corresponding portions of a plurality of pathological images that show biopsies adjacently cut from a harvested pathological tissue.

In the following example, the case that two pathological images are simultaneously displayed. However, the present disclosure can be applied to the case that three or more pathological images are simultaneously displayed.

Here, the pathological image represents digital image data that is used to perform diagnosis and that is read by a dedicated scanner from a prepared specimen made of a biopsy or sample harvested from a tissue of for example a human body.

Besides pathological images, the present disclosure can be also applied to medical images of human bodies captured through a CT, an MRI, an X ray, or the like and any non-medical images that are simultaneously displayed.

Figure 2:
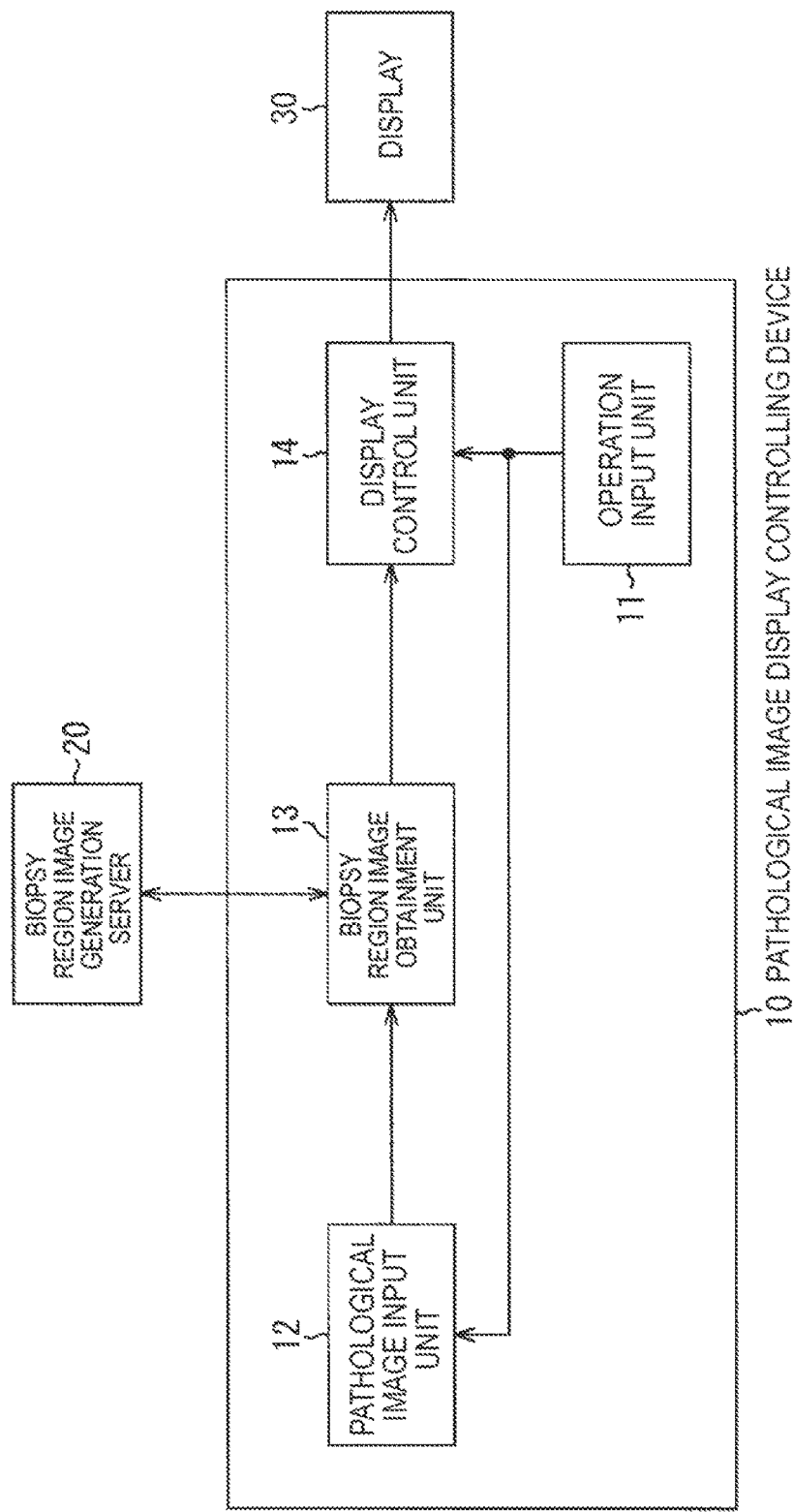
FIG. 2 is a block diagram showing an example configuration of a pathological image display control device according to an embodiment of the present disclosure.

FIG. 2 shows an example configuration of the pathological image display control device corresponding to the information processing apparatus according to the present disclosure.

The pathological image display control device 10 is composed of an operation input unit 11, a pathological image input unit 12, a biopsy region image obtainment unit 13, and a display control unit 14.

The operation input unit 11 accepts a selection operation for pathological images, various display operations, and so forth from a user (diagnostician) and outputs corresponding operation signals to the pathological image input unit 12 or the display control unit 14.

The pathological image input unit 12 inputs two pathological images PP1 and PP2 that show corresponding biopsies used for comparative diagnosis of prepared pathological images to the biopsy region image obtainment unit 13 corresponding to an operation signal based on the user's selection operation.

Figure 1:
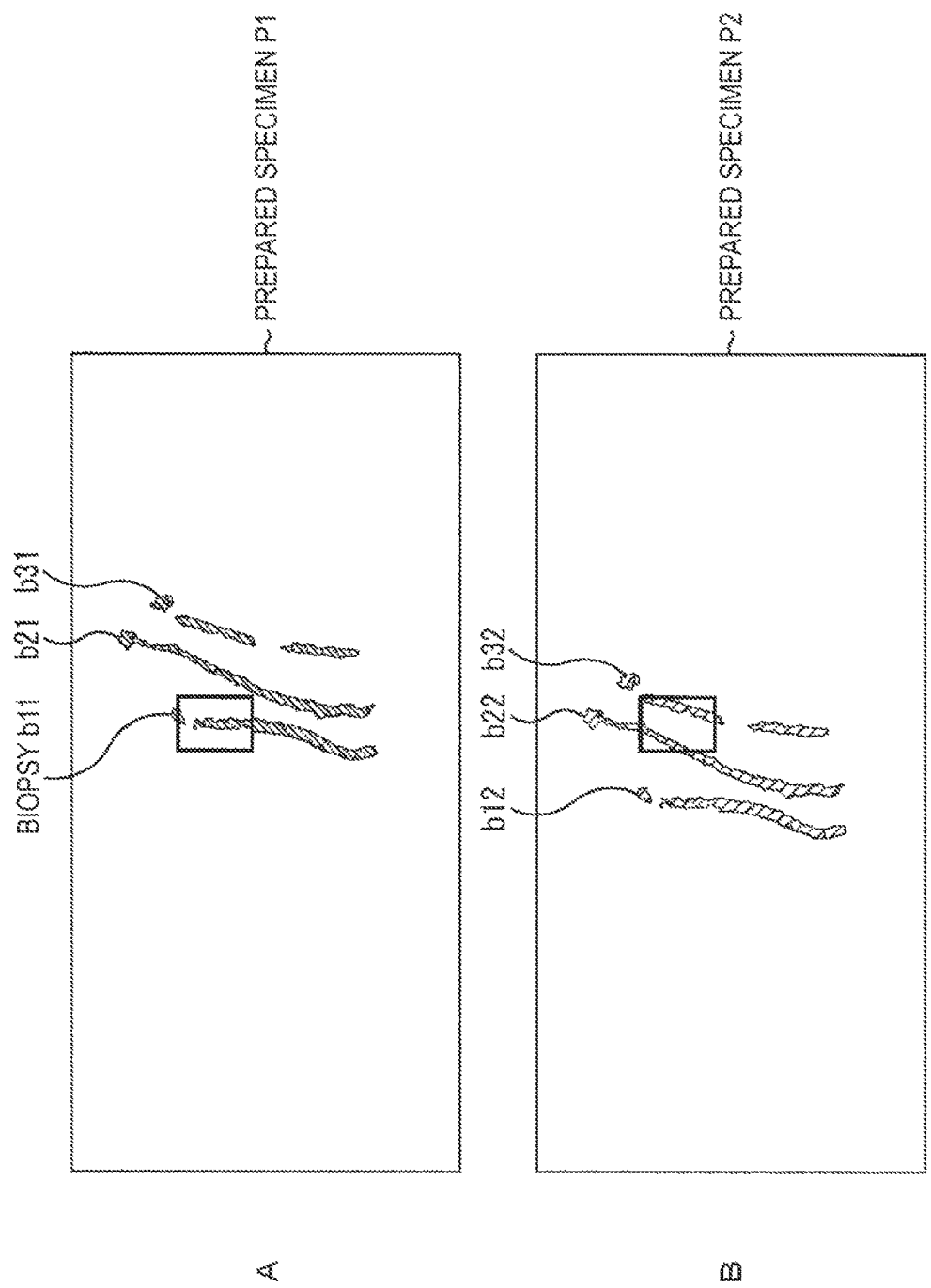
FIG. 1 is a schematic diagram showing example prepared specimens.
Figure 3:
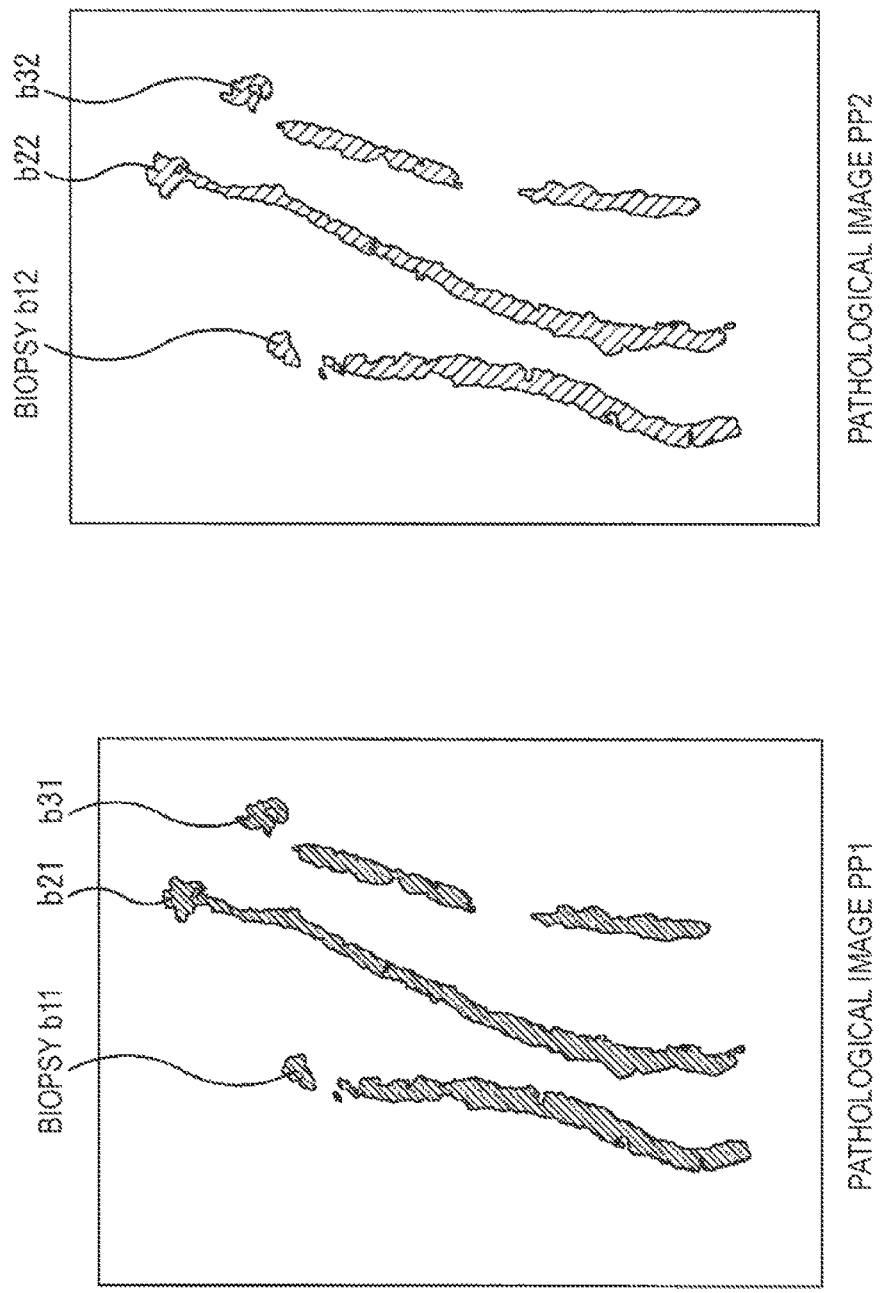
FIG. 3 is a schematic diagram showing example pathological images.

FIG. 3 shows an example of the two pathological images PP1 and PP2 that are input from the pathological image input unit 12 to the biopsy region image obtainment unit 13. These pathological images PP1 and PP2 are scanned from prepared specimens P1 and P2 shown in FIG. 1 by a scanner or the like.

The biopsy region image obtainment unit 13 sends the two pathological images to a biopsy region image generation server 20. In addition, the biopsy region image obtainment unit 13 obtains biopsy region images generated based on the two pathological images PP1 and PP2 from the biopsy region image generation server 20 and supplies the biopsy region images to the display control unit 14.

Although the biopsy region image generation server 20 is located for example on the Internet, all or part of the biopsy region image generation server 20 may be built in the pathological image display control device 10.

The biopsy region images represent images generated in such a manner that cellular tissue regions are detected from a pathological image (the entire image on the prepared specimen), the detected cellular tissue regions are grouped and extracted corresponding to the individual biopsies, and the orientations and sizes of the extracted cellular tissue regions are corrected and unified.

Corresponding to the user's operation, the display control unit 14 simultaneously displays the two biopsy region images supplied from the biopsy region image obtainment unit 13 on a display 30 located downstream of the display control unit 14. Hereinafter, the operation that causes biopsy region images to be simultaneously displayed is also referred to as the synchronous display. Various synchronous display methods that the display control unit 14 performs will be described later with reference to FIGS. 11 to 16.

Figure 4:
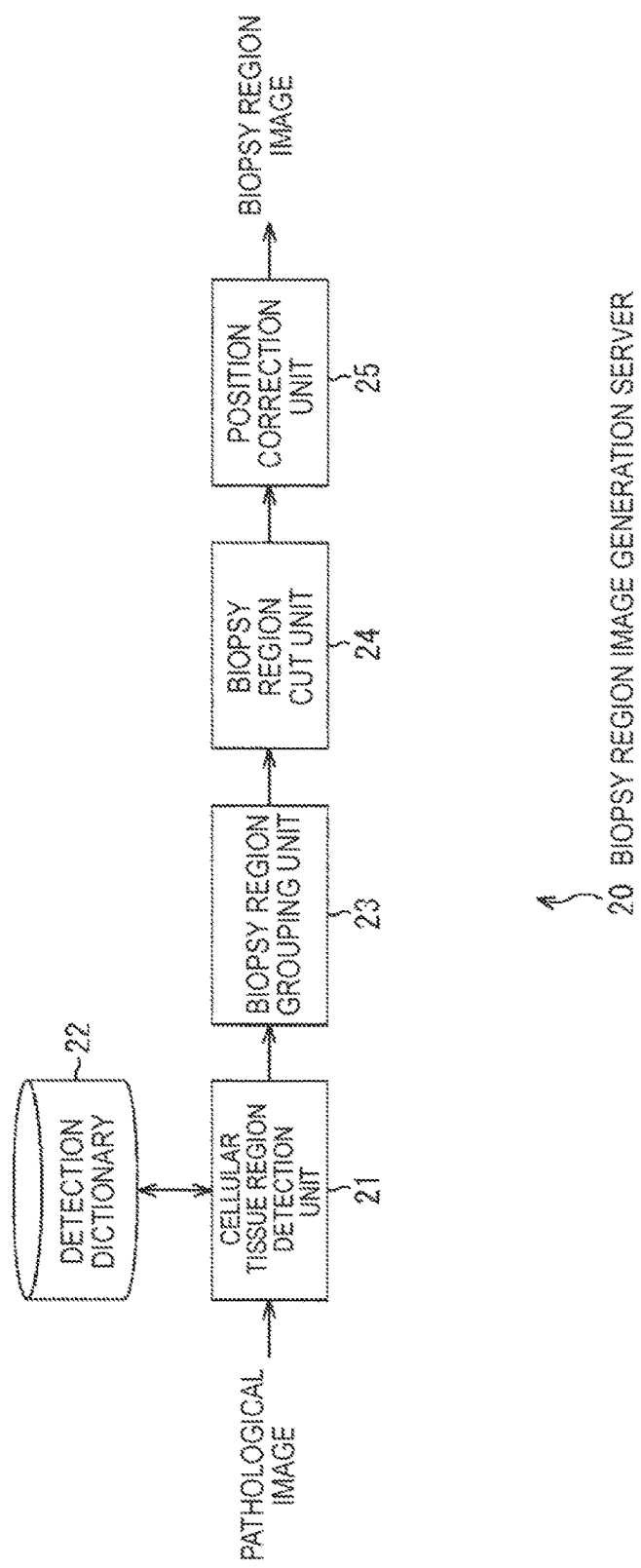
FIG. 4 is a block diagram showing an example configuration of a biopsy region image generation server.

FIG. 4 shows an example configuration of the biopsy region image generation server 20.

The biopsy region image generation server 20 is composed of a cellular tissue region detection unit 21, a detection dictionary 22, a biopsy region grouping unit 23, a biopsy region cut unit 24, and a position correction unit 25.

Consulting the detection dictionary 22, the cellular tissue region detection unit 21 detects cellular tissue regions from the entire regions of the pathological images PP1 and PP2 shown in FIG. 3 (namely, the regions of the biopsies b11, b21, and b31 shown in FIG. 3A and the regions of the biopsies b12, b22, and b32 shown in FIG. 3B).

Figure 5:
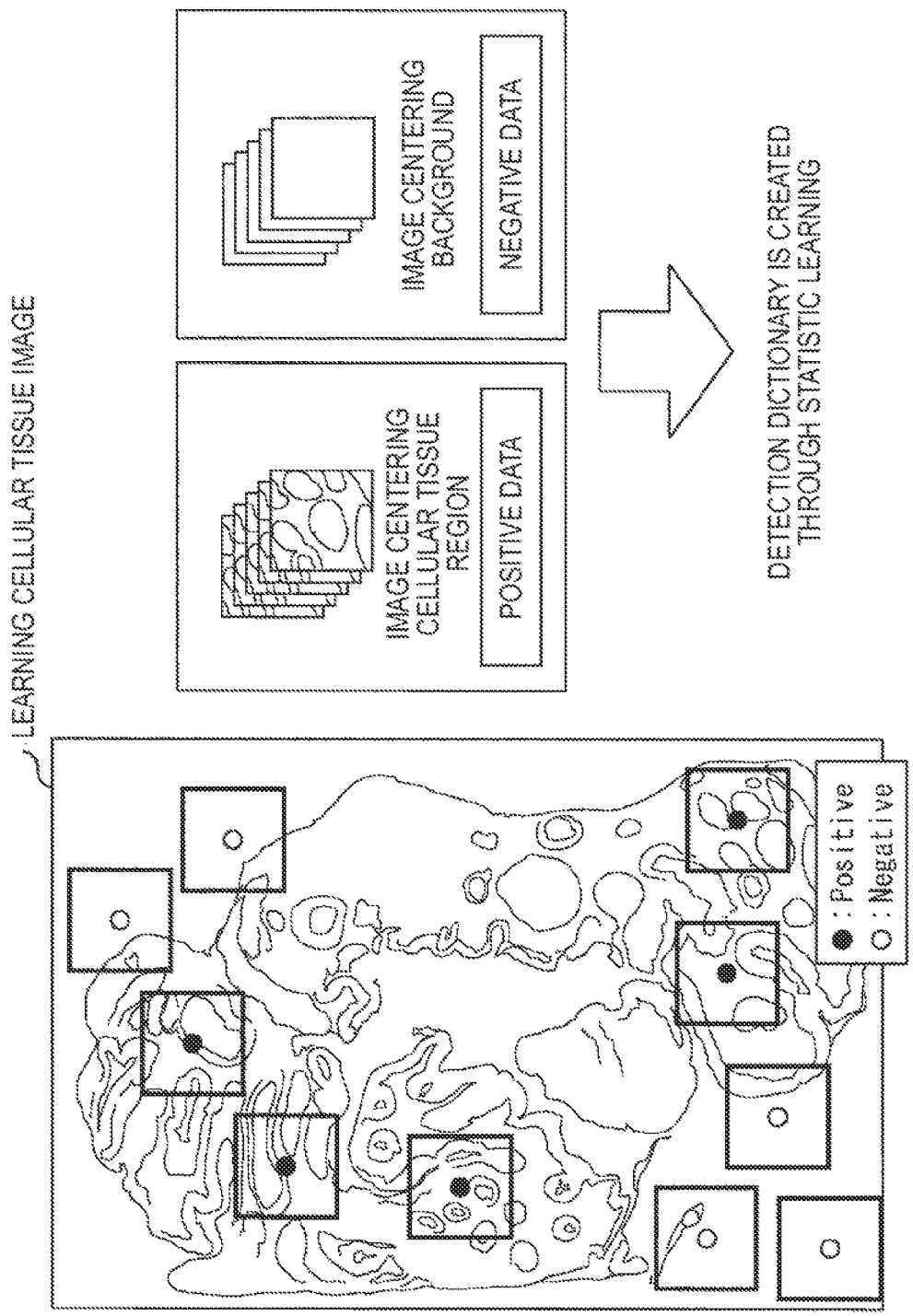
FIG. 5 is a schematic diagram describing a procedure that generates a detection dictionary.

The detection dictionary 22 is pre-generated through statistical learning using learning cellular tissue region images. The generation of the detection dictionary 22 will be described with reference to FIG. 5.

A patch image whose center is a cellular tissue region is cut from a learning cellular tissue region image and a patch image whose center is a background portion (non-cellar tissue region) are prepared as a learning data set. The image feature amounts of the learning data set are extracted. The image whose center is the cellular tissue region and the image whose center is the background portion are statistically learned as positive data and negative data, respectively.

Although the image feature amount of a patch image can be extracted by any method, the PixDif luminance differential feature amount that calculates the luminance difference of any two points on a patch image may be used as disclosed in for example JP 2005-284348A. Likewise, any statistic learning method for example Boosting may be also applied.

When the detection dictionary 22 is used, a final hypothesis F for an input patch image x can be given by Formula (1) that follows where f is a learned weak hypothesis, a is a weight, and the number of f's is T.

[Math 1]

$$F(x) = \sum_{t}^{T} \alpha_t f_t(x) \quad (1)$$

Thus, the cellular tissue region detection unit 21 cuts the input patch images whose centers are all the pixels of the pathological images PP1 and PP2, calculates the final hypothesis F for the input patch images, and performs a threshold process for the values of F so as to determine whether the center pixels of the input patch images are a positive region (cellular tissue region) or a negative region (non-cellular tissue region).

Figure 6:
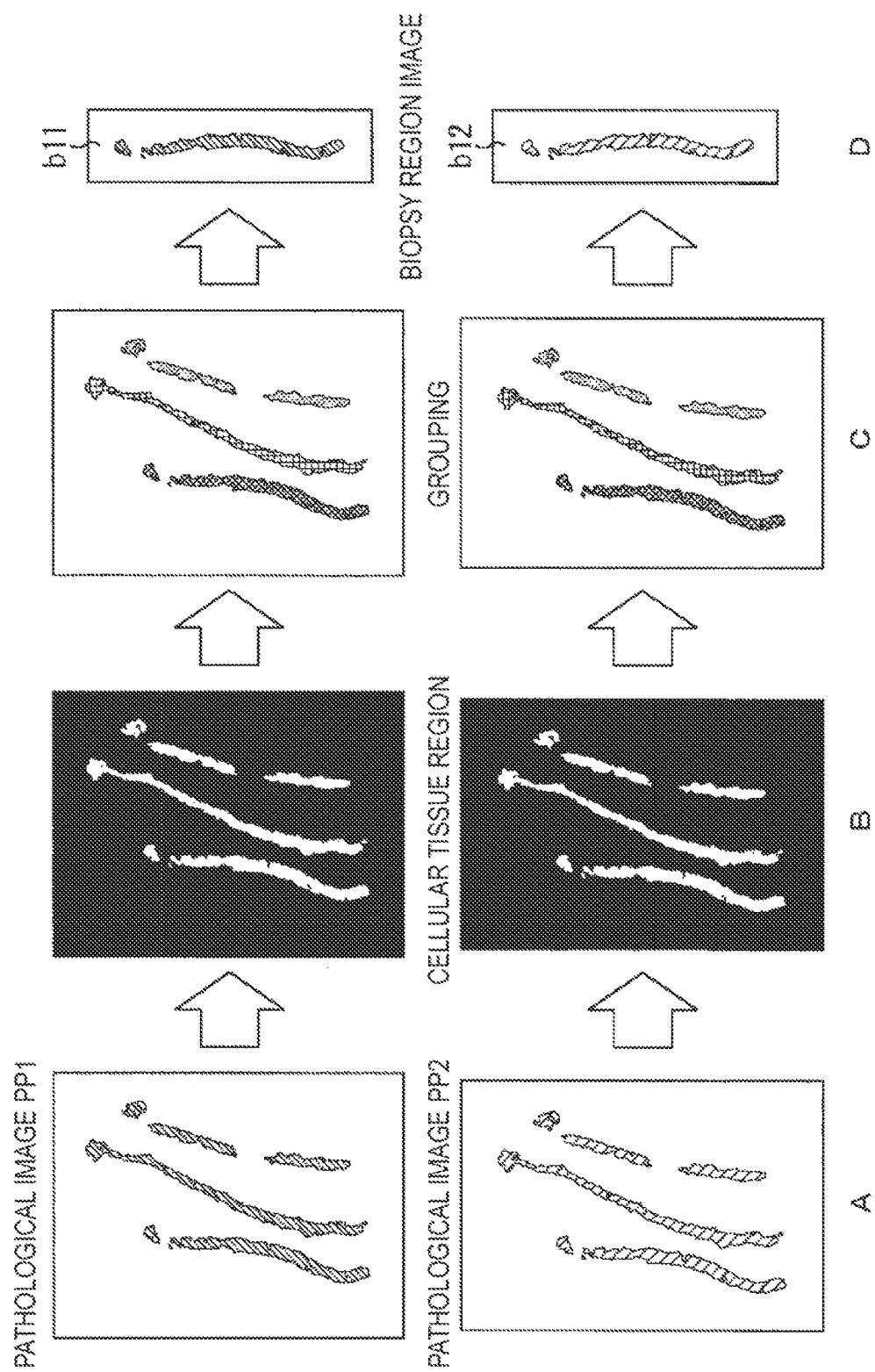
FIG. 6 is a schematic diagram describing the detection of a cellular tissue region, the grouping of tissue regions, and the cutting of the tissue regions.

The results of the cellular tissue regions that the cellular tissue region detection unit 21 detects are as shown in FIG. 6B.

Returning to FIG. 4, the biopsy region grouping unit 23 groups the cellular tissue regions detected by cellular tissue region detection unit 21 corresponding to the individual biopsies.

Specifically, pixels determined as a cellular tissue region are grouped corresponding to individual biopsy numbers that represent biopsies in the pathological images. The number of biopsies in the pathological images is known when prepared specimens are made. Thus, this grouping becomes a clustering problem in which the number of clusters is known. Next, a clustering method using spectrum clustering will be described.

It is assumed that the number of pixels in the cellular tissue region is denoted by n; the number of clusters of the target grouping (the number of biopsies) is denoted by C; and the Euclidean distance as coordinate values of a pixel i and a pixel j is denoted by $d_{ij}$.

In addition, an affinity matrix is defined as Formula (2) that follows.

[Math 2]

$$A_{ij} = \exp\left(\frac{-d_{ij}^2}{\sigma^2}\right) (i \neq j) \quad (2)$$
$$A_{ii} = 0$$

where σ is a scale parameter that is an appropriate value (for example, 0.1).

Next, a diagonal matrix D is defined as Formula (3) that follows so as to obtain a matrix L.

[Math 3]

$$D_{ii} = \sum_{j=1}^{n} A_{ij} \quad (3)$$
$$L = D^{-\frac{1}{2}} A D^{-\frac{1}{2}}$$

Next, C eigenvectors $x_1, x_2, \ldots, x_c$ are obtained in the descending order of eigenvalues of the matrix L to generate a matrix $X=[x_1, x_2, \ldots, x_c]$. Thereafter, a matrix Y of which X is normalized in each row is obtained by Formula (4) that follows.

[Math 4]

$$Y_{ij} = \frac{X_{ij}}{\left(\sum_j X_{ij}^2\right)^{\frac{1}{2}}} \quad (4)$$

When each row of the matrix Y is clustered to C element vectors by K-means, a cluster having a row number i of the matrix Y corresponds to a cluster of a pixel i.

Besides spectral clustering, the biopsy region grouping unit 23 may perform grouping using any clustering technique that directly applies K-means to input data. In this case, an appropriate clustering technique is preferably used corresponding to the characteristic of input data.

The grouped result of the biopsy region grouping unit 23 is for example, as shown in FIG. 6C, three groups that are the same as the number of biopsies, which are also the same as the number of cellular tissue regions shown in FIG. 6B.

Returning to FIG. 4 again, the biopsy region cut unit 24 corrects the rotation of the pathological image of each grouped biopsy region and cuts the corrected image.

When the rotation of the pathological image of each grouped biopsy region is corrected, a slope θ of the principal axis of inertia is given by Formula (5) that follows where a p-order moment on the x axis around the center of gravity and a q-order moment on the y axis around the center of gravity are denoted by $u_{pq}$.

[Math 5]

$$\theta = \frac{1}{2} \tan^{-1}\left(\frac{2u_{11}}{u_{20} - u_{02}}\right) \quad (5)$$

The rotation of the original pathological image is corrected by the slope θ of the principal axis of inertia. Thereafter, a white region having a predetermined width (for example, several hundred pixels) around the biopsy region is cut from the pathological image whose rotation has been corrected. As a result, a biopsy region image as shown in FIG. 6D is generated.

In FIG. 6D and the later drawings, only the biopsies b11 and b12 at the left end of the three tissues on the pathological images PP1 and PP2 are shown. However, the same process is performed for the biopsies b21 and b22 at the center of the three tissues and the biopsies b31 and b32 at the right end of the three tissues.

Figure 7:
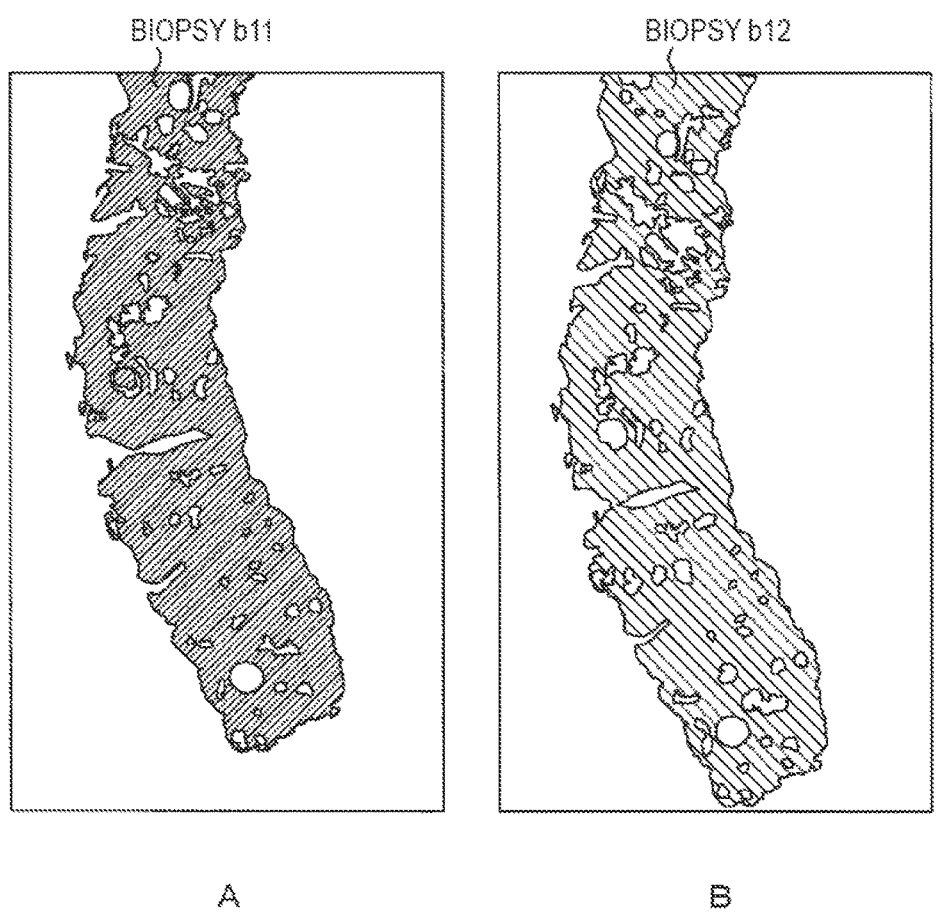
FIG. 7 is an enlarged view showing biopsy region images that have been cut.

FIG. 7 is an enlarged view of biopsy region images cut by the biopsy region cut unit 24. FIG. 7A is a biopsy region image cut from the biopsy b11 at the left end of the pathological image PP1. FIG. 7B is a biopsy region image cut from the biopsy b12 at the left end of the pathological image PP2.

As is clear from FIG. 7A and FIG. 7B, the biopsy b11 and biopsy b12 slightly deviate from each other in the vertical direction. In addition, the sizes of the biopsy b11 and biopsy b12 vary (expanded or shrunk). These vertical deviations and size variations are likely to occur depending on the pressure applied when the biopsies b11 and b12 are cut from tissues and placed on slide glasses. If the vertical deviations and/or size variations occur in the biopsy b11 and biopsy b12, it is difficult to accurately and simultaneously observe and diagnose the corresponding portions of the biopsies b11 and b12.

Figure 8:
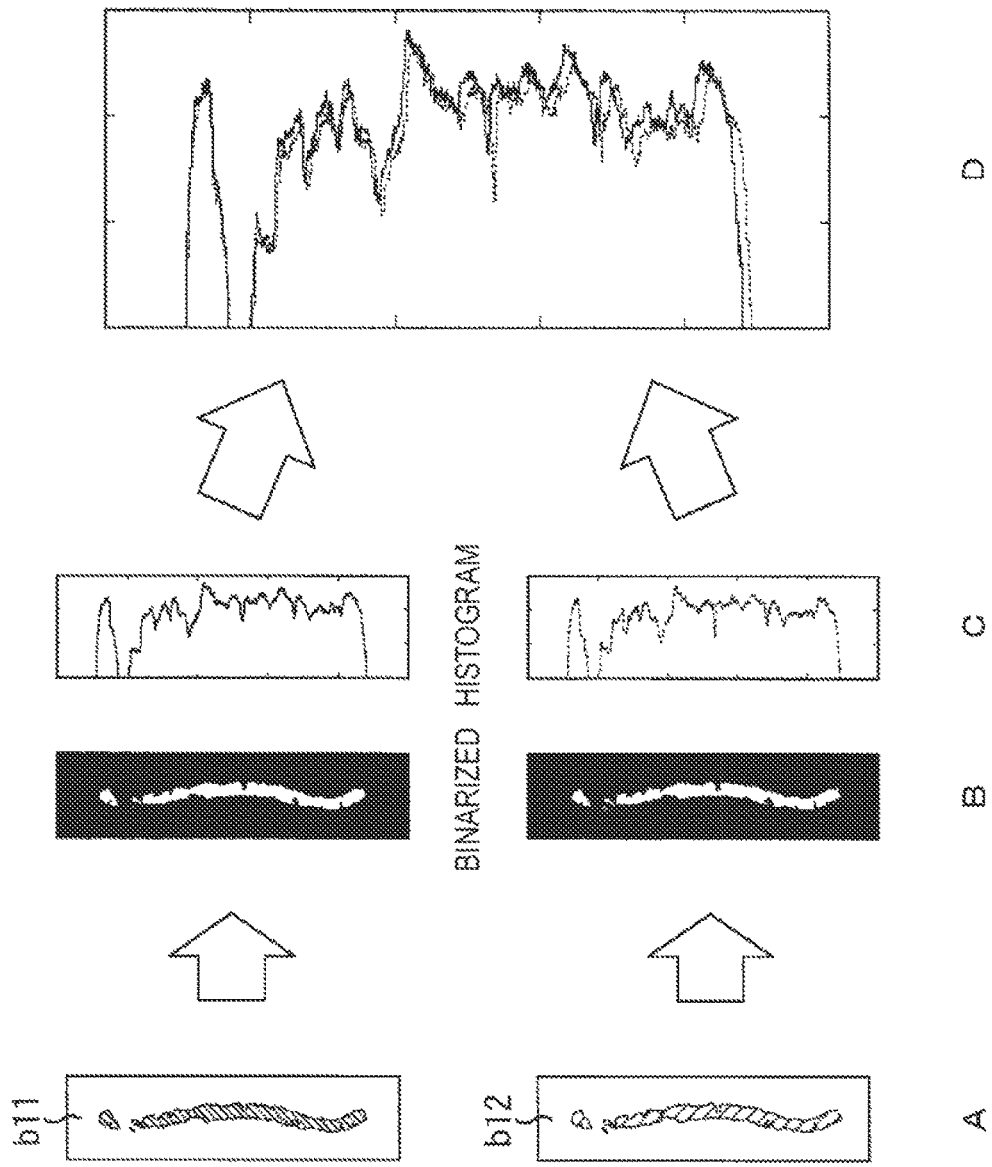
FIG. 8 is a schematic diagram describing the corrections of the positions and sizes of biopsy region images.

Thus, the position correction unit 25 located immediately downstream of the biopsy region cut unit 24 corrects and unifies the positions and sizes of the cut biopsy region images. A specific procedure will be described with reference to FIG. 8. In FIG. 8, the corrections of only vertical deviations and size variations of the biopsy region images are described. Likewise, the corrections of horizontal deviations and size variations are performed.

First, binary images that distinguish a cellular tissue region and a background (non-cellular tissue region) shown in FIG. 8B are obtained from the biopsy region images shown in FIG. 8A. Thereafter, the number of pixels in the cellular tissue region at each vertical coordinate position of the binary images is counted. Thereafter, as shown in FIG. 8C, histograms having a vertical axis that represents the vertical coordinate of each of binary images and a horizontal axis that represents the number of pixels are generated.

As shown in FIG. 8D, the two obtained histograms are superposed on each other such that while one histogram is fixed, the vertical position of the other histogram is repeatedly adjusted to enlarge or reduce the vertical size until the two histograms are sufficiently superposed on each other (specifically, a predetermined evaluation function value (for example, an inner product value) becomes a predetermined value or greater).

Figure 9:
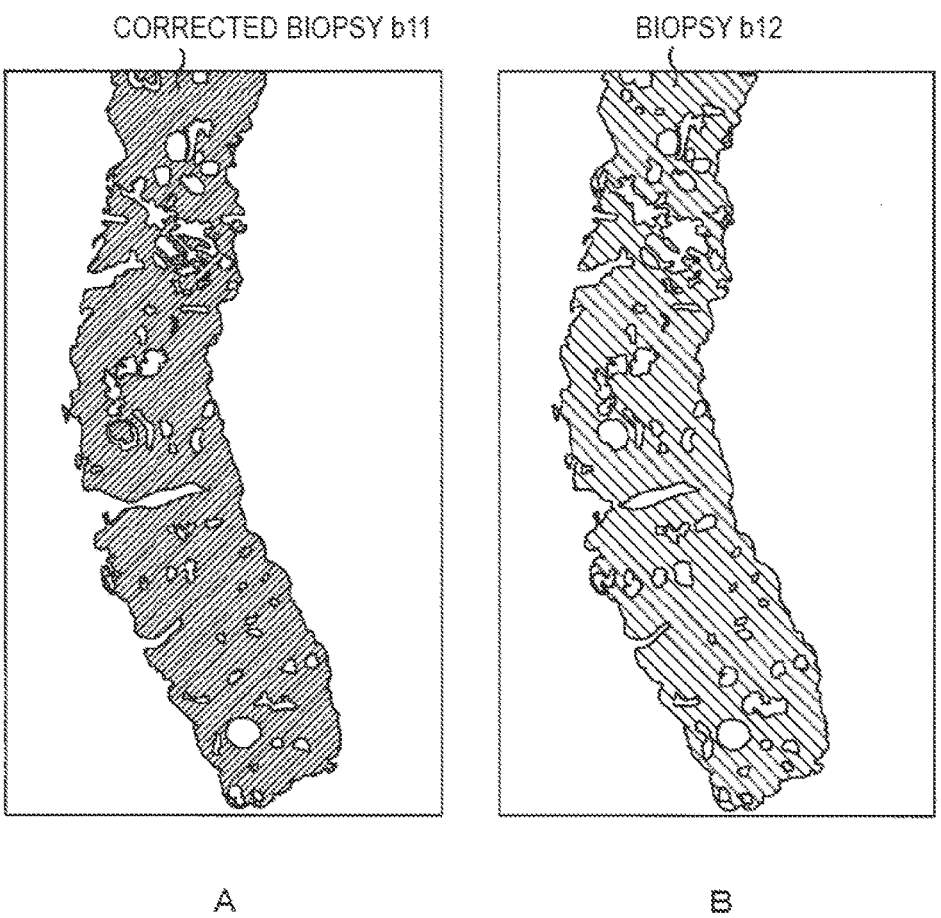
FIG. 9 is an enlarged view of corrected biopsy region images.

The adjustment values of the final vertical positions and enlarged or reduced correction values of the vertical sizes are applied to the original biopsy region images. Thus, as shown in FIG. 9, the two biopsy region images that deviate from each other are corrected to two biopsy region images that do not deviate from each other. FIG. 9 shows that the two biopsy region images that had deviated from each other shown in FIG. 7 have been corrected.

The corrected biopsy region images are returned from the biopsy region image generation server 20 to the biopsy region image obtainment unit 13.

[Operational Description]

Figure 10:
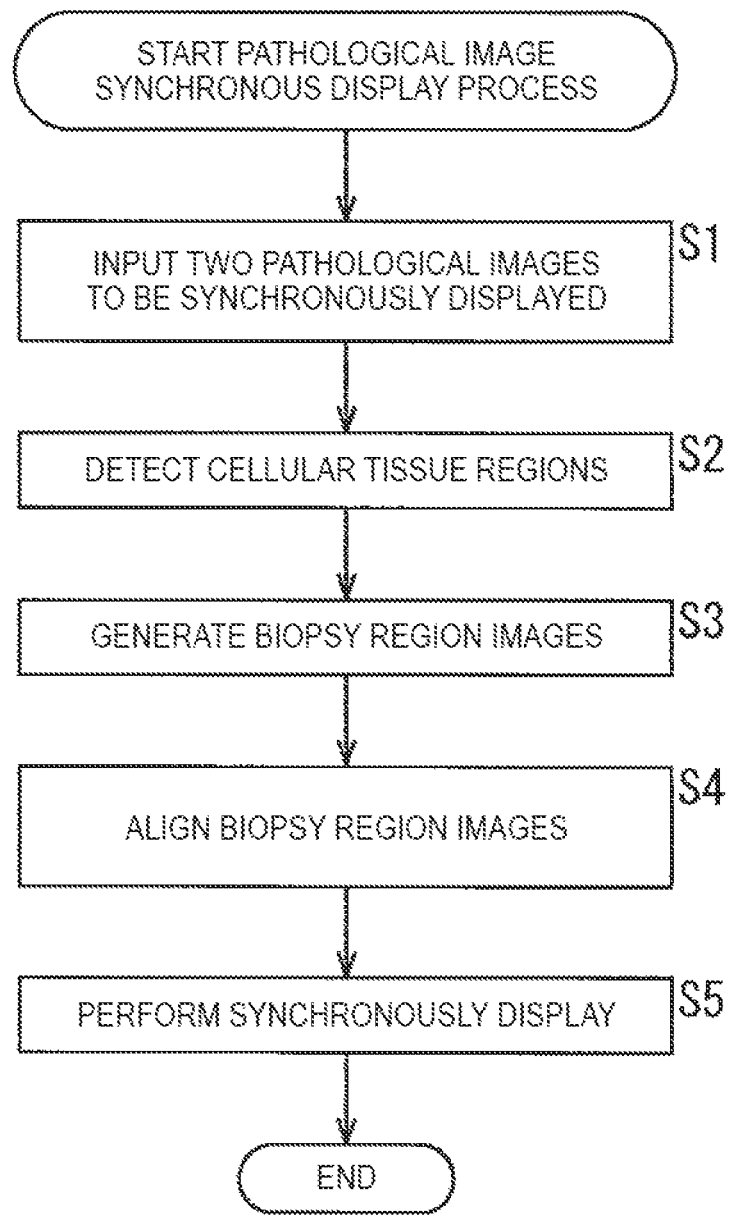
FIG. 10 is a flow chart describing a pathological image synchronous display process.

Next, the pathological image synchronous display process of the pathological image display control device 10 will be described with reference to FIG. 10. FIG. 10 is a flow chart describing the pathological image synchronous display process.

At step S1, the pathological image input unit 12 inputs two pathological images PP1 and PP2 used for comparative diagnosis to the biopsy region image obtainment section 13 corresponding to an operation signal based on a user's selective operation. The biopsy region image obtainment section 13 sends the two pathological images to the biopsy region image generation server 20.

At step S2, consulting the detection dictionary 22, the cellular tissue region detection unit 21 of the biopsy region image generation server 20 detects cellular tissue regions from the pathological images PP1 and PP2.

At step S3, the biopsy region grouping unit 23 groups the cellular tissue regions detected by the cellular tissue region detection unit 21 corresponding to the individual biopsies. The biopsy region cut unit 24 corrects the rotation of each of the grouped biopsy regions based on the slope θ of the principal axis of inertia and cuts a white region having a predetermined width (for example, several hundred pixels) around the biopsy region from the pathological image whose rotation has been corrected so as to generate a biopsy region image.

At step S4, the position correction unit 25 corrects the positions and sizes of the biopsy region images. The position correction unit 25 returns the corrected biopsy region images from the biopsy region image generation server 20 to the biopsy region image obtainment unit 13.

At step S5, the display control unit 14 causes the two biopsy region images supplied from the biopsy region image obtainment unit 13 to be synchronously displayed on the display 30 located downstream of the display control unit 14 corresponding to a user's operation. Now, the description of the pathological image synchronous display process is completed.

[Specific Examples Synchronous Displays]

Next, examples synchronous displays of the display control unit 14 will be described.

"Guide Scroll Display"

When a biopsy region image is synchronously displayed while the biopsy region image is being enlarged and vertically or horizontally scrolled, the center of the display screen is moved along the shape of the biopsy region image. For example, if the biopsy region image is formed in the "<" shape as shown in FIG. 9, when the biopsy region image is scrolled downward, the center of the screen is moved to the left and then to the right along the shape of the biopsy region image. As a result, while the user is scrolling only a portion necessary for diagnosis, he or she can always observe the portion.

"Automatic Vertical/Horizontal Division Selection Display"

When the shape of the biopsy region in an biopsy region image is portrait, a screen 50 is divided in the vertical direction and the two divided biopsy region images are horizontally and simultaneously displayed as shown in FIG. 11A. When the shape of the biopsy region in a biopsy region image is landscape, a screen 60 is horizontally divided in the horizontal direction and the two divided biopsy region images are vertically and simultaneously displayed as shown in FIG. 11B. As a result, since the biopsy region displayed on the screen is widened, the user can easily observe and diagnose the biopsy region.

Whether the biopsy region is portrait or landscape depends on the angle (slope) of the principal axis of inertia of the biopsy region. Assuming that the upward vertical direction is 0 degree and the counterclockwise direction is the positive angle direction, when the angle of the principal axis of inertia is from −45 degrees to +45 degrees or from 130 degrees to 225 degrees, the biopsy region is displayed as a portrait region; otherwise, the biopsy region is displayed as a landscape region.

"Instantaneous Switch Display"

A biopsy region image 70 shown in FIG. 12A and a biopsy region image 71 shown in FIG. 12B may be instantaneously switched between the biopsy region image 70 and the biopsy region image 71 on the display corresponding to a user's predetermined operation. When this display method is used, since the user can see these biopsy region images with less movement of his or her viewpoint than the user simultaneously sees two images simultaneously displayed, he or she can easily compare the corresponding portions of the two biopsy region images.

"Cut and Placement Display"

When the user specifies a selection region 81 having any size on a biopsy region image 80 that shows the tissue b11 as shown in FIG. 13A, a cut display region 83 is displayed adjacent to the selection region 81 as shown in FIG. 13B. The cut display region 83 shows a portion of the tissue b12 corresponding to a portion of the tissue b11 specified in the selection region 81. The user can freely move the display position of the cut display region 83 from the neighborhood of the selection region 81. In addition, the user can freely move the selection region 81 of the biopsy region image 80. As the selection region 81 is moved, the cut display region 83 is also moved. As a result, the portion of the tissue b12 displayed in the cut display region 83 is changed. This display method allows the user to place portions he or she wants to compare at his or her desired positions.

"Leaf-Though Display"

When the user specifies a selection region 92 having any size on a biopsy region image 91 that shows the tissue b11 and performs a predetermined operation (such as a mouse dragging or the like) for the selection region 92 as shown in FIG. 14A, the portion of the tissue b11 displayed in the selection region 81 is gradually changed to the portion of the tissue b12 as shown in FIG. 14B. This display method allows the user to compare the corresponding portions of the tissue b11 and the tissue b12 without necessity of moving his or her viewpoint. In addition, the ratio of regions to be compared can be adjusted corresponding to a user's operational amount (such as mouse's dragging amount).

"Multiple Staining Color Combining Display"

A plurality of immunohistochemistries (IHCs) are performed for a plurality of corresponding biopsies as shown in FIG. 15A. Stained portions (FIG. 15B) are superposed on a biopsy region image stained by H&E (FIG. 15C). As a result, a plurality of IHC and H&E results may be simultaneously displayed as shown in FIG. 15D. Thus, the user can observe the IHC and H&E results at the same time and perform diagnosis. Alternatively, a plurality of IHC stained portions (FIG. 15B) that differ in stained colors may be combined and displayed without superposing the stained portions on the H&E stained biopsy region image (FIG. 15C).

"Relevant Comment Display"

The user can add a diagnostic comment 111 about a predetermined portion of a biopsy region image that shows one biopsy b11 of the above described "instantaneous switch display" on the screen. When a biopsy region image 112 that shows the other biopsy b12 is displayed, the diagnostic comment 111 made corresponding to the biopsy b11 is added to the corresponding portion of the biopsy b12. Thus, the user can check the portion of the biopsy b12 corresponding to the portion of the biopsy b11 he or she has diagnosed.

As described above, the pathological image display control device 10 according to an embodiment of the present disclosure can synchronously display a plurality of images.

Specifically, since corresponding portions of a plurality of images can be simultaneously displayed, the user can improve his or her diagnosing accuracy. Compared with the case that one biopsy is stained by a plurality of different staining methods and their colors are separated, a multiply stained image can be synchronously displayed in high quality. In addition, since a process that corrects the positions and sizes of a plurality of biopsy region images is performed, corresponding images can be displayed without positional deviations.

In addition, staining methods that are normally performed at the same time can be used in combinations so as to synchronously display images. In addition, a combination of images captured by a dark field observation, a bright field observation, and a phase-contrast observation cannot be simultaneously observed by ordinary microscopes can be synchronously displayed.

As the foregoing effect, the user (diagnostician) can improve his or her diagnosing accuracy and shorten the diagnosing time.

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 12:
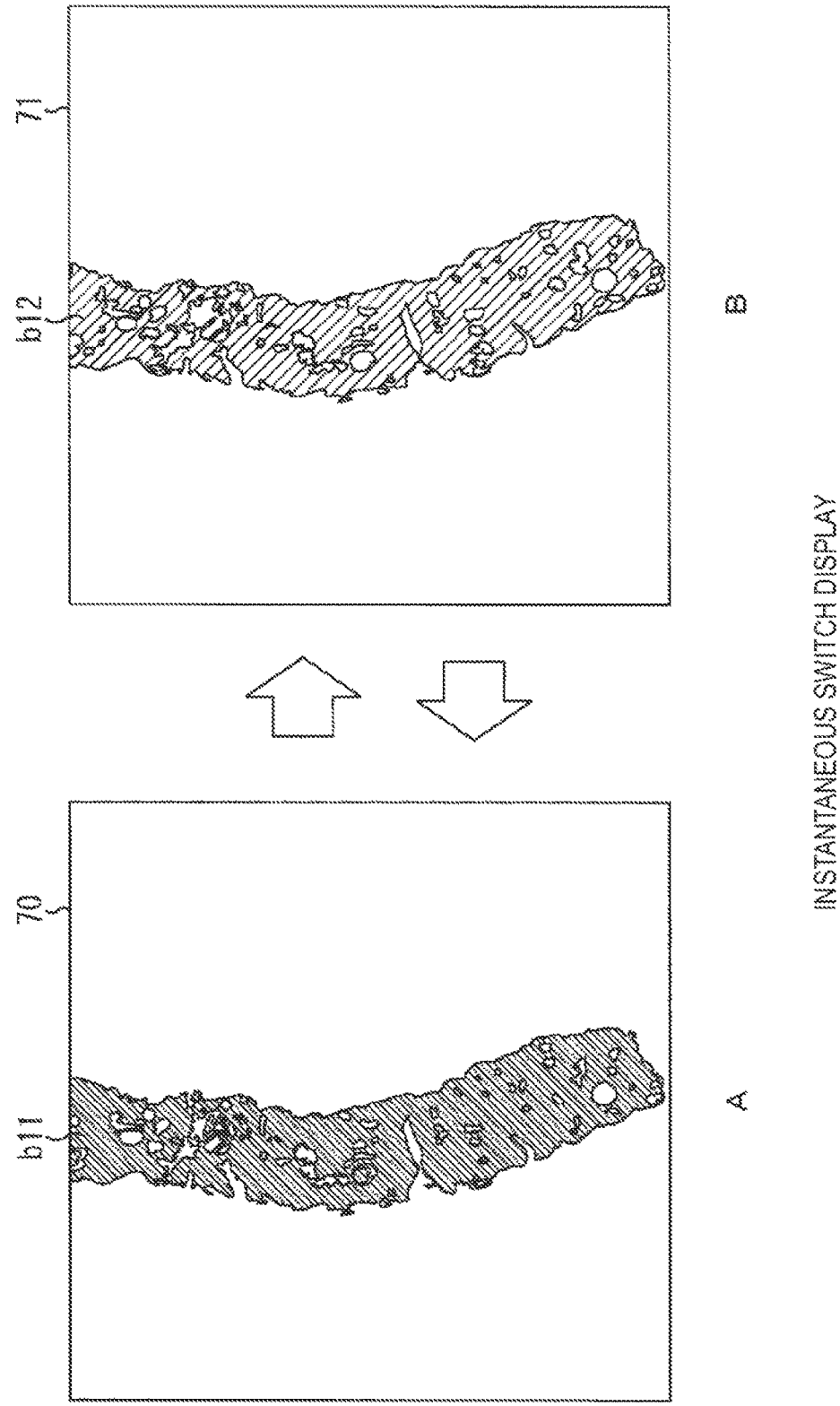
FIG. 12 is a schematic diagram showing an example screen shot of an instantaneous switch display.

FIG. 12 is a block diagram showing an example configuration of the hardware of a computer that executes the series of processes described earlier according to a program.

In the computer 200, a central processing unit (CPU) 201, a read only memory (ROM) 202 and a random access memory (RAM) 203 are mutually connected by a bus 204.

An input/output interface 205 is also connected to the bus 204. An input unit 206, an output unit 207, a storing unit 208, a communication unit 209, and a drive 210 are connected to the input/output interface 205.

The input unit 206 is configured from a keyboard, a mouse, a microphone, or the like. The output unit 207 configured from a display, a speaker or the like. The storing unit 208 is configured from a hard disk, a non-volatile memory or the like. The communication unit 209 is configured from a network interface or the like. The drive 210 drives a removable medium 211 such as a magnetic disk, an optical disk, a magneto-optical disk, a semiconductor memory or the like.

In the computer configured as described above, the CPU 201 loads a program that is stored, for example, in the recording unit 208 onto the RAM 203 via the input/output interface 205 and the bus 204, and executes the program. Thus, the above-described series of processing is performed.

A program that the computer (CPU 201) executes can be provided as a so-called web application that allows the computer to access for example a predetermined server on the Internet to obtain the program.

By inserting the removable medium 211 into the drive 210, the program can be installed in the recording unit 208 via the input/output interface 205. Further, the program can be received by the communication unit 209 via a wired or wireless transmission media and installed in the storing unit 208. Moreover, the program can be installed in advance in the ROM 202 or the recording unit 208.

It should be noted that the program executed by a computer may be a program that is processed in time series according to the sequence described in this specification or a program that is processed in parallel or at necessary timing such as upon calling.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 10 pathological image display control device
11 operation input unit
12 pathological image input unit
13 biopsy region image obtainment unit
14 display control unit
20 biopsy region image generation server
21 cellular tissue region detection unit
22 detection dictionary
23 biopsy region grouping unit
24 biopsy region cut unit
25 position correction unit
30 display
200 computer
201 CPU

The invention claimed is:

1. An information processing apparatus comprising:
an operation input unit for accepting a user input selection operation;
an input unit for acquiring a first image and a second image in response to the user input selection operation;
a processor; and
a memory device, the memory device storing instructions that cause the processor to:
extract a plurality of areas in which a specific object is present from the first image and the second image by using a third image having a center that is a background portion and a fourth image having a center that is a portion other than the background portion, wherein the third image and the fourth image are part of a learning data set that is used to statistically learn as positive data an image whose center is a cellular tissue region and statistically learn as negative data an image whose center is a background portion,
classify the plurality of areas into groups by image pattern,
select a first area of the first image and a second area of the second image which are in a same group, and
control display of the first area and the second area such that display of the second area is adjusted in at least one of orientation, position, and size based on the first area, wherein controlling display of the first area and the second area comprises controlling display of the first area and the second area so that the first area and the second area are displayed synchronously so as to facilitate comparison of the first area and the second area.

* * * * *